United States Patent
Köhler et al.

(10) Patent No.: US 6,435,717 B1
(45) Date of Patent: Aug. 20, 2002

(54) X-RAY DEVICE

(75) Inventors: Thomas Köhler, Norderstedt; Volker Rasche, Hamburg; Jörg Sabczynski, Norderstedt, all of (DE)

(73) Assignee: Koninklijke Phillips Electronics N.V., Eindhoven (NL)

( * ) Notice: Subject to any disclaimer, the term of this patent is extended or adjusted under 35 U.S.C. 154(b) by 0 days.

(21) Appl. No.: 09/661,721

(22) Filed: Sep. 14, 2000

(30) Foreign Application Priority Data

Sep. 14, 1999 (DE) .......................... 199 43 898

(51) Int. Cl.$^7$ .............................. A61B 6/08
(52) U.S. Cl. ..................... 378/206; 378/205; 378/63
(58) Field of Search ............... 378/205, 206, 378/63

(56) References Cited

U.S. PATENT DOCUMENTS

| | | | |
|---|---|---|---|
| 4,618,980 A | * 10/1986 | Lescrenier et al. | ......... 378/206 |
| 5,136,627 A | * 8/1992 | Conrads et al. | ............. 378/206 |
| 5,539,798 A | * 7/1996 | Asahina et al. | ............ 378/98.5 |
| 5,873,826 A | 2/1999 | Gono et al. | ................. 600/425 |

FOREIGN PATENT DOCUMENTS

| | | | |
|---|---|---|---|
| EP | 0819407 A1 | 1/1998 | ............ A61B/6/10 |
| JP | 747063 A | 2/1995 | ............ A61B/6/08 |
| JP | 8266535 A | 10/1996 | ............ A61B/6/08 |
| JP | 8336518 A | 12/1996 | ............ A61B/6/00 |

* cited by examiner

*Primary Examiner*—Robert H. Kim
*Assistant Examiner*—Jurie Yun
(74) *Attorney, Agent, or Firm*—John Vodopia

(57) ABSTRACT

The invention relates to an X-ray device, notable a device for X-ray fluoroscopy, which includes an X-ray source and an X-ray detector for the continuous formation of X-ray images of a patient (5) from an invariable position of the X-ray source (2) and the X-ray detector (3). The invention includes indicator means for illuminating and/or monitoring essentially the radiation zone over the patient which is traversed by X-rays. This offers the advantage that for the physician it quasi visualizes or monitors the radiation zone which is traversed by X-rays during a treatment with simultaneous formation of X-ray images so that the physician can make sure that he or she, notably his or her hands, is not inadvertently exposed to a continuous X-ray dose.

14 Claims, 2 Drawing Sheets

X-RAY DEVICE

BACKGROUND OF THE INVENTION

1. Field of the Invention

The invention relates to an X-ray device, notably a device for X-ray fluoroscopy, which includes an X-ray source and an X-ray detector for the continuous formation of X-ray images of a patient from an invariable position of the X-ray source and the X-ray detector.

2. Description of the Related Art

X-ray devices of this kind are often used as an aid for monitoring surgical interventions performed on a patient. To this end, X-ray images of the examination zone of interest are continuously formed from a fixed position of the X-ray source and the X-ray detector; these images are displayed on-line on a monitor so that the attending physician can directly follow the intervention taking place. A problem is encountered, however, in that parts of the body of the physician, notably the hands, inadvertently and unobtrusively invade the zone between the patient and the X-ray source or the X-ray detector which is traversed by the invisible X-rays, so that the physician is also exposed to an X-ray dose. Despite the comparatively low dose incurred when invading the X-ray beam once, in the long term the hands of the physician could suffer in the case of frequent exposure.

U.S. Pat. No. 5,873,826 discloses a computed tomography device which includes a rotating X-ray source and a rotating X-ray detector and is provided with a light source which is arranged directly adjacent the X-ray source and also rotates. In order to prevent the hands of the attending physician from being exposed to an excessive X-ray dose, steps are taken such that the X-rays are switched off in a first angular range in which the hands of the physician normally work, the X-rays being switched on only in a second angular range (the remainder). In order to let the physician know the angular range in which the X-rays are switched off, this range is illuminated by means of the light source, the light source being switched off in the remaining angular range (or vice versa). Moreover, the deactivation of the X-ray source in the first angular range also ensures that the quality of the X-ray image is not degraded by the hands of the physician.

OBJECTS AND SUMMARY OF THE INVENTION

It is an object of the present invention to improve an X-ray device of the kind set forth by taking steps for the protection of the attendant staff.

This object is achieved by means of an X-ray device including an x-ray source and x-ray detector for continuous formation of X-ray images of a patient from an unvariable position of the X-ray source and the X-ray detector, and indicator means for illuminating and/or monitoring essentially the radiation zone over the patient which is transversed by X-rays.

In the CT device which is known from U.S. Pat. No. 5,873,826 only the zone between the X-ray source and the patient in a given angular range is visible to the physician and protected against X-rays; the zone between the X-ray detector and the patient, however, is not visible and not protected even when the X-ray detector is situated over the patient and the hand of the physician is working between the detector and the patient. In the X-ray device according to the invention, however, adjustment is made to the zone above the patient, irrespective of the position of the X-ray source and the X-ray detector, because the hands of the physician are normally present therein during an intervention. For example, in the case of a C-arm X-ray device the X-ray source occupies a position underneath the patient and the X-ray detector is situated over the patient, so that in such an X-ray device the indicator means are preferably provided on the X-ray detector so as to illuminate and monitor the radiation zone between the X-ray detector and the patient. In the X-ray device according to the invention the X-ray source is not switched off either in a given angular range or when the hand of the physician is in the radiation zone, because in that case image acquisition from a fixed position of X-ray source and the X-ray detector could not produce instantaneous X-ray images and hence monitoring of the intervention by the physician would be impossible. It is rather the responsibility of the physician himself or herself whether to invade the illuminated and/or monitored radiation zone with his or her hands; in the X-ray device in accordance with the invention, however, he or she is informed immediately when he or she does so.

Advantageous embodiments are disclosed notably in the further claims. The indicator means are preferably formed as optical indicator means for quasi-visualization of the zone traversed by the X-rays, as optical monitoring means for monitoring an intervention in the radiation zone and/or as acoustic alarm means for producing an acoustic alarm signal upon invasion of the radiation zone.

BRIEF DESCRIPTION OF THE DRAWINGS

The invention will be described in detail hereinafter with reference to the drawing. Therein.

DETAILED DESCRIPTION OF THE INVENTION

Figure 1:
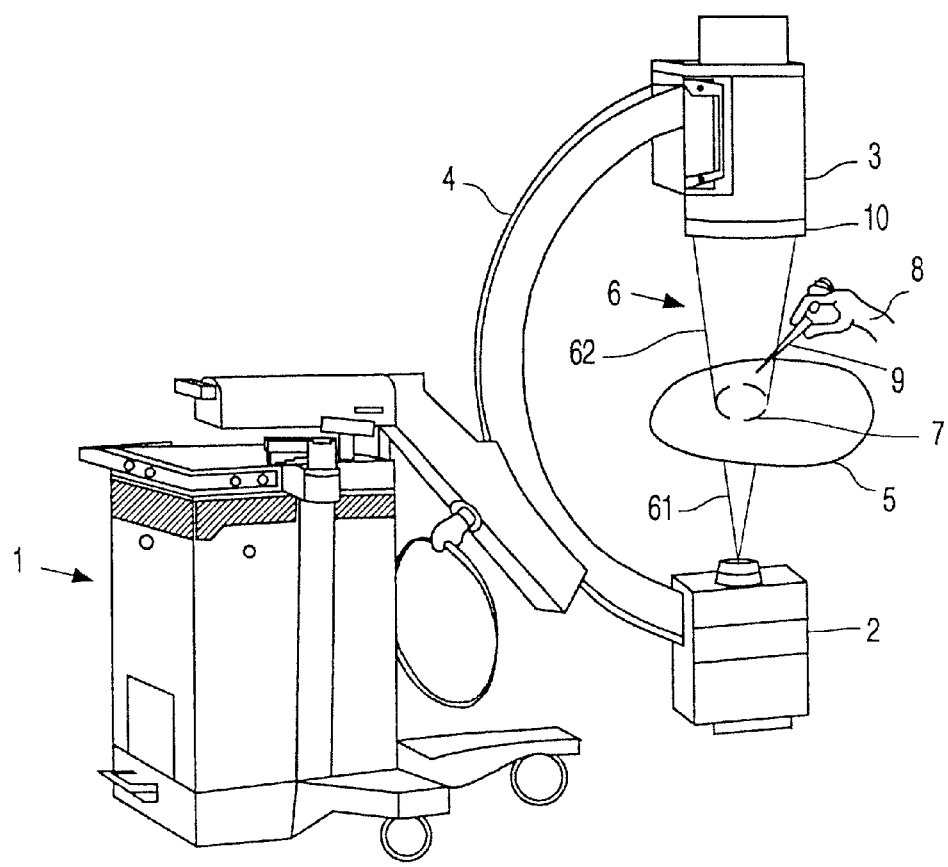
FIG. 1 shows an X-ray fluoroscopy device according to the invention during an intervention.

The device 1 for X-ray fluoroscopy which is shown in FIG. 1 includes an X-ray source 2 and an X-ray detector 3, both of which are mounted on a C-arm 4. In the normal operating position shown, the X-ray source 2 is situated underneath a symbolically represented patient 5 while the X-ray detector 3 is situated over the patient 5. The reference numeral 6 denotes X-rays in the form of a conical X-ray beam (beam 61 underneath the patient 5 and beam 62 above the patient 5) which traverses the patient 5 in the examination zone 7. Also shown symbolically is the hand 8 of a physician who performs an intervention on the patient 5 by means of a medical instrument 9, for example a scalpel or a biopsy needle, and wishes to follow this intervention directly on a monitor (not shown); to this end, X-ray images are formed continuously by the X-ray device 1. Moreover, on the lower side of the X-ray detector 3 which faces the patient 5 there are provided indicator means 10 which serve to visualize or monitor for the physician the radiation zone 62 which is traversed by X-rays between the X-ray detector 3 and the patient 5.

Figure 2:
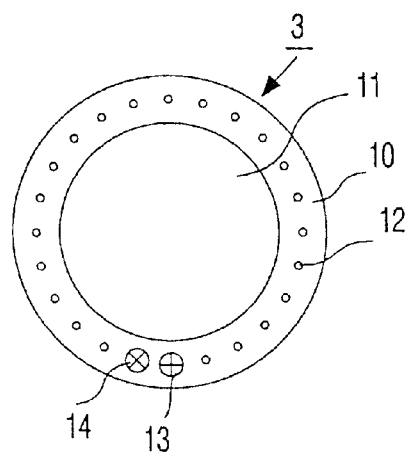
FIG. 2 is a plan view of an X-ray detector with indicator means.

As is shown in greater detail in the plan view of the lower side of the X-ray detector 3 in FIG. 2, the indicator means 10 include a plurality of laser diodes 12 which are arranged in an annular configuration around the detector surface 11. The radiation direction of these laser diodes 12 is oriented towards the focus of the X-ray source 2, so that essentially the contour of the X-ray beam 62 is illuminated. The embodiment shown is also provided with an infrared light emitting diode 13 and an infrared detector 14 which monitor the described radiation zone 62 in conformity with the principle of a motion detector and output a signal when the hand 8 of the physician or an instrument 9 enters the radiation zone 62.

Instead of using a plurality of laser diodes 12, it is also possible to use other illumination means such as, for example, a single laser diode with a plurality of light beams, a plurality of optical conductors or a UV radiation device which irradiates the radiation zone 62 with ultraviolet light; in that case the physician should wear fluorescent gloves or the instruments for treatment should be constructed so as to be fluorescent. It is of essential importance, however, that the indicator means are oriented to the focus of the X-ray tube 2 and hence illuminate or monitor the radiation zone 62 as accurately as possible so that the physician can immediately notice his entry of the radiation zone 62, either because the physician sees this directly or because an additional optical or acoustic alarm signal is given. The number and the arrangement of the laser diodes 12 or the IR diode 13 and the IR detector 14 shown in FIG. 2 are given merely by way of example and can be chosen in conformity with the type and performance of the indicator means used or with the X-ray device equipped with such means.

Figure 3:
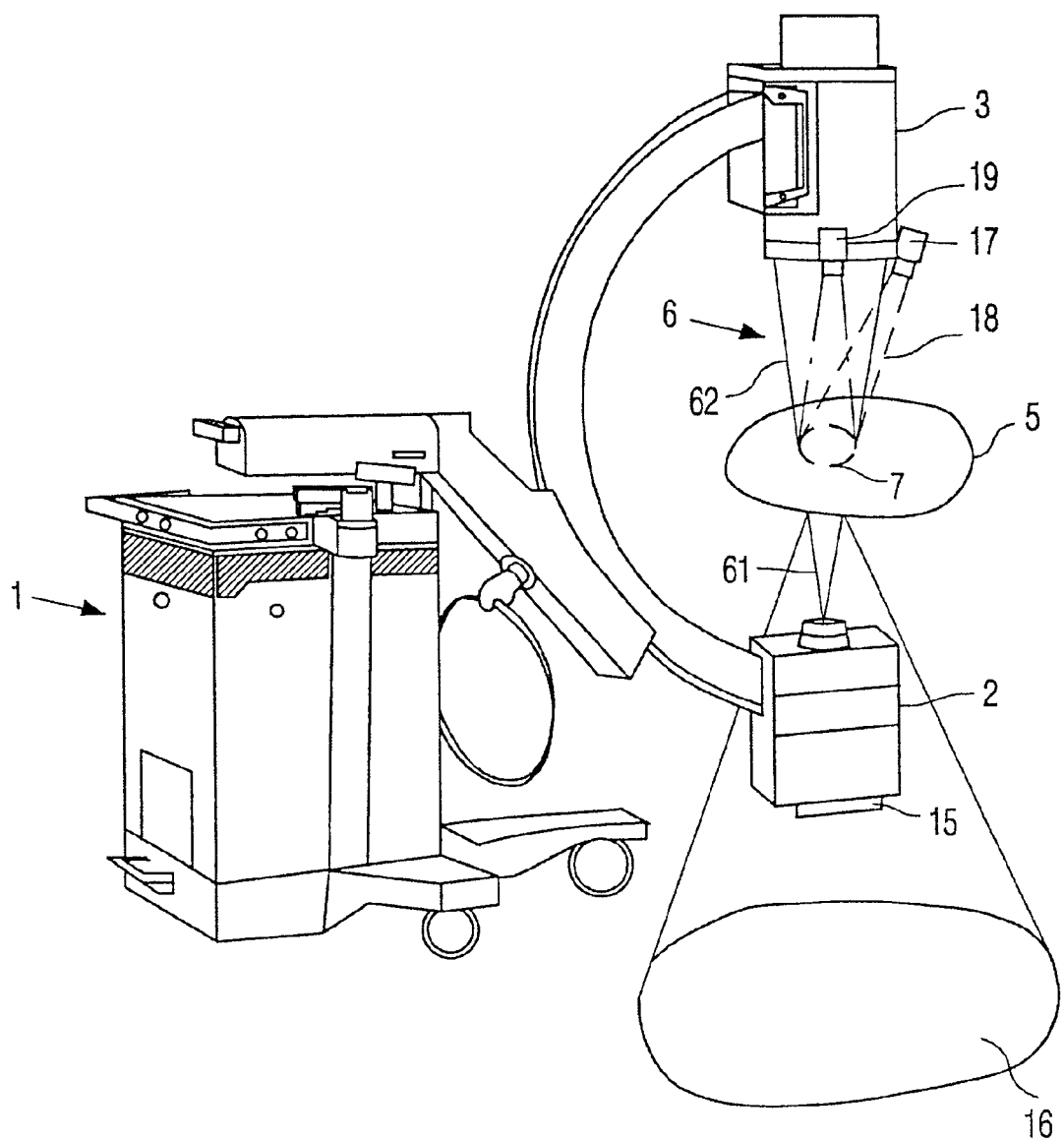
FIG. 3 shows a further embodiment of a device for X-ray fluoroscopy according to the invention.

FIG. 3 shows a further embodiment of an X-ray device for fluoroscopy according to the invention. This embodiment utilizes indicator means in the form of a video camera 17 which essentially optically monitors a monitoring zone 18 which is not identical to the X-ray zone 62 but always registers therewith (the closer one is to the patient 5) and coincides therewith approximately in the examination zone 7. The video camera 17 is constructed, for example in such a manner that it is capable of detecting motions in the monitoring zone 18 so as to output a relevant signal, or that the image picked up by the video camera is superposed on the X-ray monitor or a separate monitor. The detector device 3 in this embodiment is additionally provided with a further camera 19 which can project the instantaneous X-ray image on the surface of the patient 5 in the examination zone 7, thus forming another surgical aid for the physician.

X-rays emanate from the X-ray source 2 in essentially one main direction in the X-ray devices shown, so vertically towards the detector in the FIGS. 1 and 3. A further amount of scattered radiation which is too large to be ignored is generated in the patient 5 and emitted essentially at an angle of 180° relative to the main direction, so from the body 5 in the direction of the X-ray source 2 in said Figures. In the case of frequent exposure these X-rays may also cause damage to the body, that is to the feet of the physician in the position of the X-ray source shown, in as far as it is not shielded from the X-ray source. In order to visualize and monitor this preferred scattered radiation range also for the physician, an indicator means 15 with an illumination and/or monitoring zone 16 is mounted on the lower side of the X-ray source 2 in the embodiment shown in FIG. 3. The indicator means 15 may be constructed in the same way as the previously mentioned indicator means; the illumination or monitoring zone should correspond as well as possible to the zone with the most scattered radiation, viewed in this direction from the X-ray source 2. The physician can thus recognize the zone in which scattered radiation preferably occurs or is given a warning when parts of his body, for example the feet, are present in said scattered radiation zone.

The invention is not restricted to the use in the device shown for X-ray fluoroscopy with a C-arm, but can in principle be used in any X-ray device, so also in, for example, a permanently installed X-ray device. Furthermore, instead of being mounted on the X-ray detector, the indicator means can also be mounted on the X-ray source or on both elements, particularly when the X-ray source is arranged over the patient. It is also possible to combine a plurality of different indicator means so as to increase the safety for the physician.

Moreover, the indicator means may be constructed so that they can be adapted to the geometry of the X-ray beam, notably to the magnitude of the angle of aperture of the X-rays. To this end, for example, a signal for changing the aperture of a diaphragm which is mounted on the X-ray source and is intended to change the beam geometry can also be applied to the indicator means so that the means can be oriented in such a manner that their illumination or monitoring zone is adapted to the changed radiation zone. In the case where they make the radiation zone quasi-visible, the indicator means can also be used to indicate (prior to the formation of X-ray images) the examination zone that will be irradiated, so that the physician can adapt and optimize the irradiated zone without it being necessary to switch on the X-rays.

What is claimed is:

1. An X-ray device which includes an X-ray source and an X-ray detector for the continuous formation of X-ray images of a patient from an invariable position of the X-ray source and the X-ray detector, and indicator means for automatically illuminating and monitoring the radiation zone over the patient which is traversed by X-rays.

2. An X-ray device as claimed in claim 1, wherein the indicator means is arranged on one of: the X-ray detector and the X-ray source.

3. An X-ray device as claimed in claim 1, wherein the indicator means include optical illumination means comprising at least one of: a plurality of laser diodes, optical conductors and a UV radiation device, which illumination means are arranged in the radiation zone over the patient which is traversed by X-rays.

4. An X-ray device as claimed in claim 1, wherein the indicator means includes optical monitoring means comprising at least one of: an infrared transmitter and an infrared detector, and a video camera, for monitoring the radiation zone over the patient which is traversed by X-rays.

5. An X-ray device as claimed in claim 4, wherein the indicator means includes an acoustic alarm device for producing an acoustic alarm signal when an object enters the monitored radiation zone.

6. An X-ray device as claimed in claim 1, wherein the indicator means includes a device for projecting the instantaneous X-ray image onto the surface of the patient (5) which is traversed by X-rays.

7. An X-ray device as claimed in claim 1, wherein further indicator means are arranged on the X-ray source in such a manner such that the zone which is traversed by X-rays from the X-ray source in the direction opposing the main direction is illuminated and/or monitored.

8. An X-ray device as claimed in claim 1, wherein the illumination or monitoring zone of the indicator means can be adapted to the beam geometry.

9. An X-ray device as claimed in claim 8, wherein said illumination or monitoring zone can be adapted to the angle of aperture of the X-rays.

10. An X-ray device as claimed in claim 2, wherein the indicator means include optical illumination means comprising at least one of: a plurality of laser diodes, optical conductors and a UV radiation device, which indicator means are arranged in the radiation zone over the patient which is traversed by X-rays.

11. An X-ray device as claimed in claim 2, wherein the indicator means include optical monitoring means comprising at least one of: an infrared transmitter and an infrared detector, and a video camera, for monitoring the radiation zone over the patient which is traversed by X-rays.

12. An X-ray device as claimed in claim 3, wherein the indicator means include optical monitoring means comprising at least one of: an infrared transmitter and an infrared detector, and a video camera, for monitoring the radiation zone over the patient which is traversed by X-rays.

13. An X-ray device as claimed in claim 4, wherein the indicator means includes an acoustic alarm device for producing an acoustic alarm signal when an object enters the monitored radiation zone.

14. An X-ray device as claimed in claim 12, wherein the indicator means includes an acoustic alarm device for producing an acoustic alarm signal when an object enters the monitored radiation zone.

* * * * *